US005294341A

United States Patent [19]

Fukazawa

[11] Patent Number: 5,294,341

[45] Date of Patent: Mar. 15, 1994

[54] METHOD FOR SEPARATION OF β-AMYLASE

[75] Inventor: Chikafusa Fukazawa, Tsukuba, Japan

[73] Assignee: Director of National Food Research Institute, Ministry of Agriculture, Forestry and Fisheries, Tokyo, Japan

[21] Appl. No.: 974,178

[22] Filed: Nov. 10, 1992

[30] Foreign Application Priority Data

Feb. 7, 1992 [JP] Japan .................................... 4-56052

[51] Int. Cl.[5] .............................................. B01D 15/08

[52] U.S. Cl. .................................... 210/635; 210/656; 127/55; 435/95; 435/201; 536/103

[58] Field of Search ..................... 210/635, 656, 198.2, 210/502.1; 435/99, 95, 101, 201, 202, 204; 127/55; 536/102, 127

[56] References Cited

U.S. PATENT DOCUMENTS 4,539,399 9/1985 Armstrong ....................... 210/502.1
4,781,858 11/1988 Mizukami ............................ 210/635
4,867,884 9/1989 Rendleman .......................... 210/635
5,080,795 1/1992 Pirkle .................................. 210/643
5,104,547 4/1992 Cabrera ............................ 210/198.2
5,190,663 3/1993 Fetzer ................................. 210/674
5,204,254 4/1993 Schmid ............................. 435/320.1

*Primary Examiner*—Ernest G. Therkorn
*Attorney, Agent, or Firm*—Frishauf, Holtz, Goodman & Woodward

[57] ABSTRACT

Disclosed is a method of separating β-amylase from a solution containing β-amylase, in which the solution is treated with an α-cyclodextrin fixed water-insoluble high polymer compound in the presence of ammonium sulfate to form an adsorbed composite of the high polymer compound and β-amylase and soluble impurities not adsorbed to the high polymer compound are separated and removed. By the method, a high-purity β-amylase, which is highly useful in the starch saccharification industry, may specifically and efficiently be isolated from a β-amylase-containing mixture solution.

3 Claims, No Drawings

METHOD FOR SEPARATION OF β-AMYLASE

FIELD OF THE INVENTION

The present invention relates to a method of separation of β-amylase. It is known that β-amylase exists in plants such as soybeans, wheat, barley and sweet potatoes and in microorganisms of the genera Bacillus and Clostridium. Of them, β-amylase from soybeans, wheat and barley is widely used for preparation of maltose syrup in starch saccharification industry, due to the property thereof of forming maltose from α-1,4-glucan.

BACKGROUND OF THE INVENTION

Soybeans, wheat and barley contain α-amylase in addition to β-amylase. In order to remove the α-amylase, a method of deactivating α-amylase by varying the ambient pH and temperature or by using a chelating agent has heretofore been used. However, since complete removal of α-amylase by the method is accompanied by deactivation of β-amylase, it is difficult to completely remove α-amylase by the method in view of the yield of β-amylase.

On the other hand, in the starch saccharification industry, production of a high-purity maltose syrup is being advanced and therefore a high-purity β-amylase which does not produce any other saccharides to be derived from α-amylase than maltose is needed.

There is known affinity chromatography as a method of rapid and specific purification of enzyme proteins. In accordance with the method, only the intended enzyme is specifically adsorbed to an insoluble carrier having a substrate of the enzyme or a substrate analogue thereof as fixed thereto so that the soluble impurities are removed from the enzyme, whereby only the intended substance (enzyme) is specifically and rapidly separated and purified.

Some reports have already been disclosed, regarding affinity chromatography of β-amylase. For instance, Per Vretblad (FEBS Letters, 47 (1974) 86–89) reported that β-amylase from sweet potatoes is specifically adsorbed to a Sepharose column having α-cyclodextrin, which is a β-amylase antagonistic inhibitor, as fixed thereto, whereupon a bovine serum albumin, which has been added to the column simultaneously as a model of an impurity protein, is not adsorbed to the column and may therefore be removed from β-amylase, and that the adsorbed β-amylase may specifically be eluted from the column by adding α-cyclodextrin to the eluent. A. Hoschke et al. (Starch, 28 (1976), 426–432) reported, though not explicitly referring to the origin, that β-amylase adsorbs to a Sepharose column having α-cyclodextrin as fixed thereto.

However, recently, K. Subbaramiah et al. (Starch, 41, (1989) 357–359) disclosed a different report mentioning that when they prepared Sepharose having cyclodextrin as fixed thereto by the same method as the above mentioned Per Vretblad's method (FEBS Letters, 47, 1974), any β-amylase derived from sweet potatoes, potatoes and malt did not adsorb it.

Under the situation, we the present inventors prepared and examined an α-cyclodextrin-fixed Sepharose column in accordance with the Per Vretblad's report (FEBS Letters, 47, 1974) and found that β-amylase derived from soybeans and malt, which has an important role in the starch saccharification industry, does not adsorb to the carrier. At present, therefore, there is no report relating to specific affinity chromatography of β-amylase derived from soybeans and malt.

Under the above-mentioned conditions, we the present inventors earnestly investigated affinity chromatography for adsorbing β-amylase derived from soybeans and malt, which has an important role in the starch saccharification industry, and, as a result, have found that such β-amylase which does not adsorb to the α-cyclodextrin-fixed carrier in the presence of a buffer or the like may efficiently adsorb to thereto by adding ammonium sulfate to the solution to be applied to the column. On the basis of the finding, we have completed the present invention.

SUMMARY OF THE INVENTION

Specifically, the present invention provides a method of separating β-amylase from a β-amylase-containing solution, in which the solution is treated with a water-insoluble high polymer compound having α-cyclodextrin as fixed thereto in the presence of ammonium sulfate to form an adsorbed complex of the said high polymer compound and β-amylase, and soluble impurities which do not adsorb to the high polymer compound are separated and removed.

The β-amylase separation method of the present invention is characterized in that β-amylase is adsorbed to an α-cyclofextrin-fixed carrier in the presence of ammonium sulfate. Regarding affinity chromatography of α-amylase, it is known that α-amylase may efficiently adsorb to starch by addition of an organic solvent such as ethanol or a salt of several kinds having a salting-out effect thereto. Being different from the known technique, only ammonium sulfate is effective in the method of the present invention, and the fact has not been reported up to the present.

DETAILED DESCRIPTION OF THE INVENTION

The present invention will be explained in more detail by way of some preferred embodiments of it.

The ligand to which β-amylase adsorbs in the affinity chromatography of the present invention, as a means for separating β-amylase by the present invention, is α-cyclodextrin which is a β-amylase antagonistic inhibitor. The carrier to be used for fixing α-cyclodextrin thereto is not specifically defined and any desired water-insoluble high polymer compound can be used. For instance, preferred is agarose gel or the like. Particularly, epoxy-activated Sepharose 2B, 4B or 6B (product of Pharmacia Co.), epoxy-activated Toyopearl (product of Toso Co.) epoxy-activated Bio-gel A-5m, A-15m or A-150m (Biorad Co.) and the like are preferable. In addition, a crosslinked product of cyclodextrin itself, such as cyclodextrin polymer, may also be used as the insoluble carrier.

The concentration of ammonium sulfate to be used in adsorption of β-amylase is preferably higher only within the range where the proteins in the solution are not salted out, so as to attain a higher effect. In general, it is 0.5M or more, more preferably 1M or more. However, if it is more than 2M, proteins would precipitate out in the enzyme solution of some kind. Therefore, the upper limit of the concentration of ammonium sulfate is may be elevated to such a degree that would not cause precipitation of proteins in the solution (generally, up to 2M or so).

The adsorption method is not specifically defined, and either a batch process or a column process may be employed. Elution of the adsorbed enzyme may well be effected in a suitable solution not containing ammonium sulfate. The adsorbed enzyme may be eluted with a solution containing α-cyclodextrin.

The present invention will be explained in more detail by way of the following examples, which, however, are not intended to restrict the scope of the present invention.

PRODUCTION EXAMPLE 1

Fixation of α-cyclodextrin to carrier

Various carriers may be employed, to which α-cyclodextrin is fixed. In the present example, used was a hydrophilic high polymer carrier agarose gel (Sepharose, trade name by Pharmacia Co.) for the purpose of reducing as much as possible the influence of the carrier to adsorption. Fixation was effected in the manner mentioned below. Precisely, 4 g of an epoxy-activated Sepharose (produced by Pharmacia Co.) was suspended and swollen in 25 ml of water, and swelling and suction filtration of the suspension was repeated with 400 ml of water. Finally, this was washed with 25 ml of 0.1M NaOH. The activated carrier as washed previously was added to a solution of 300 mg of α-cyclodextrin as dissolved in 12 ml of 0.1M NaOH and shaken at 45° C. for 16 hours. After completion of the reaction, the reaction liquid was filtered, and the adsorbed substance was washed with 100 ml of water, 200 ml of 2.5% glucose solution, 100 ml of water, 100 ml of 0.5M NaCl-containing 0.1M boric acid buffer (pH 8.0) and 100 ml of 0.5M NaCl-containing 0.1M acetic acid buffer (pH 4.0) in this order, to prepare α-cyclodextrin Sepharose.

EXAMPLE 1

Adsorption of Soybean β-amylase to α-cyclodextrin Sepharose from Various Solutions 1 ml of α-cyclodextrin Sepharose was equilibrated with a solution as shown in Table 1 below, and 3 ml of a solution prepared by dissolving 500 units of crude β-amylase as extracted from defatted soybeans in the same solution as that used for equilibration of α-cyclodextrin Sepharose was added thereto and shaken in a chilled room (4° C.) for one hour, whereby βamylase was batchwise adsorbed to α-cyclodextrin Sepharose.

Afterwards, the non-adsorbed parts were washed out with the same solution, and 50 mM acetic acid buffer (pH 5.7) was added and shaken for 30 minutes to elute the adsorbed enzyme. Next, by measuring the activity of the fraction, the adsorption activity unit of β-amylase as adsorbed to one ml of α-cyclodextrin Sepharose was obtained. The reason why the salt concentration of each kind varied in adsorption is because the solubility of the salts was taken into consideration. Measurement of the activity was effected, using a soluble starch as a substrate, in 50 mM acetic acid buffer (pH 5.7) at 37° C., whereupon the amount of producing one μmol of maltose in one minute was defined to be one unit (U). The results obtained are shown in Table 1 below.

TABLE 1

| Buffer Used in Adsorption Reaction | Adsorption Activity* (U) |
|---|---|
| 50 mM Acetic Acid Buffer (pH 5.7) | 1 |
| 1M Ammonium Sulfate-containing 50 mM Acetic Acid Buffer (pH 5.7) | 117 |
| 1M Ammonium Nitrate-containing 50 mM Acetic Acid Buffer (pH 5.7) | 7 |
| 1M Sodium Nitrate-containing 50 mM Acetic Acid Buffer (pH 5.7) | 3 |
| 0.5M Sodium Sulfate-containing 50 mM Acetic Acid Buffer (pH 5.7) | 5 |
| 10% Ethanol-containing 50 mM Acetic Acid Buffer (pH 5.7) | 4 |
| 2M Sodium Chloride-containing 50 mM Acetic Acid Buffer (pH 5.7) | 4 |
| 50 mM Acetic Acid Buffer (pH 5.7) Containing 1M Ammonium Sulfate and 0.1% (W/V) α-cyclodextrin | 6 |

From Table 1 above, it is understood that the soybean β-amylase did not almost adsorb to the cyclodextrin-fixed Sepharose in the presence of any other salt solution, alcohol-containing buffer or buffer only, than ammonium sulfate. Therefore, the β-amylase as adsorbed to the fixed carrier in an ammonium sulfate solution may easily be eluted out from it merely by removing ammonium sulfate therefrom. Since soybean β-amylase did not adsorb to the cyclodextrin-fixed Sepharose in a buffer containing α-cyclodextrin and 1M ammonium sulfate, it is understood that the soybean β-amylase adsorbed to the carrier due to the affinity of the enzyme to α-cyclodextrin but not to the carrier of itself.

EXAMPLE 2

Adsorption of Malt-Derived and Sweet Potato-Derived β-amylase to α-cyclodextrin Sepharose One ml of α-cyclodextrin Sepharose was equilibrated with 50 mM acetic acid buffer containing 1M ammonium sulfate or not containing it. To each was added 3 ml of a solution prepared by dissolving 500 units of crude β-amylase as extracted from malt or sweet potato-derived β-amylase standard product (product by Sigma was de-salted) in the same solution as that used for equilibration of α-cyclodextrin Sepharose, and the resulting mix was shaken in a chilled room for one hour whereby β-amylase was adsorbed to α-cyclodextrin Sepharose.

Afterwards, the non-adsorbed parts were washed out with the same solution, and 50 mM acetic acid buffer containing 1% (W/V) cyclodextrin was added and shaken for 30 minutes to elute the adsorbed enzyme. By measuring the activity of the fraction, the binding activity unit of β-amylase to one ml of α-cyclodextrin Sepharose was obtained. Measurement of the activity was effected, using a soluble starch as a substrate, in 50 mM acetic acid buffer at 37° C., whereupon the amount of producing one μmol of maltose in one minute was defined to be one unit (U). All the buffers used for malt-derived β-amylase had pH of 5.2 and those for sweet potato-derived β-amylase had pH of 4.8 The results obtained are shown in Table 2 below.

TABLE 2

| Kind of β-amylase | Adsorption Activity (U) | |
|---|---|---|
| | Only Acetic Acid Buffer | Acetic Acid Buffer Containing 1M Ammonium Sulfate |
| Malt | 3 | 122 |
| Sweet Potato | 114 | 142 |

From Table 2 above, it is understood that the malt-derived β-amylase did not adsorb to the carrier in the absence of 1M ammonium sulfate, like the above-mentioned soybean-derived β-amylase. Regarding the sweet potato-derived β-amylase, it is understood from Table 2 that the β-amylase adsorbed to the carrier only in a buffer, as so reported by Per Vretblad (FEBS Letters, 47 (1974) 86–89), but it adsorbed further more effectively in 1M ammonium sulfate.

EXAMPLE 3

Influence of Concentration of Ammonium Sulfate on Adsorbability of Soybean β-amylase to α-cyclodextrin Sepharose One ml of α-cyclodextrin Sepharose was equilibrated with a solution as shown in Table 3 below, and 3 ml of a solution prepared by dissolving 500 units of crude β-amylase as extracted from defatted soybeans in the same solution as that used for equilibration of α-cyclodextrin Sepharose was added thereto and shaken in a chilled room for one hour, whereby β-amylase was adsorbed to α-cyclodextrin Sepharose. Afterwards, the non-adsorbed parts were washed out with the same solution, and 50 mM acetic acid buffer (pH 5.7) was added and shaken for 30 minutes to elute the adsorbed enzyme. Next, by measuring the activity of the fraction, the binding activity unit of β-amylase to one ml of α-cyclodextrin Sepharose was obtained. Measurement of the activity was effected in the same manner as in Example 1. The results obtained are shown in Table 3 below.

TABLE 3

| Ammonium Sulfate | Adsorption Activity (U) |
|---|---|
| 0.5 | 17 |
| 1.0 | 119 |
| 2.0 | 158 |

From the results of Table 3 above, it is understood that the adsorption activity becomes higher with elevation of the concentration of the ammonium sulfate and that the concentration is suitably at least 0.5M or more, more preferably 1.0M or more, for attaining effective adsorption. Regarding the upper limit of the concentration, it may be more than 2.0M to further elevate the adsorption yield. However, if the concentration is too high, proteins would precipitate in the enzyme solution of some kinds and addition of ammonium sulfate with a too high concentration would be unfavorable.

In accordance with the present invention, a high-purity β-amylase, which is highly useful in the starch saccharification industry, may specifically and efficiently be isolated from a β-amylase-containing mixture solution.

While the invention has been described in detail and with reference to specific embodiments thereof, it will be apparent to one skilled in the art that various changes and modifications can be made therein without departing from the spirit and scope thereof.

What is claimed is:

1. A method of separating β-amylase from a solution containing β-amylase, which comprises treating said solution with an α-cyclodextrin fixed water-insoluble high polymer compound in the presence of ammonium sulfate to form an adsorbed composite of the high polymer compound and β-amylase and separating soluble impurities not adsorbed to the high polymer compound to remove the impurities.

2. The method of separating β-amylase as claimed in claim 1, wherein the concentration of ammonium sulfate is from 0.5 to 2.0M.

3. The method of separating β-amylase as claimed in claim 1, wherein said water-insoluble high polymer compound is agarose gel.

* * * * *

UNITED STATES PATENT AND TRADEMARK OFFICE
CERTIFICATE OF CORRECTION

PATENT NO. : 5,294,341

DATED : March 15, 1994

INVENTOR(S) : FUKAZAWA

It is certified that error appears in the above-identified patent and that said Letters Patent is hereby corrected as shown below:

Title page, left column, [73] Assignee: after "Fisheries," delete "Tokyo, Japan" and insert --Ibaraki, Japan--.

Signed and Sealed this

Twenty-fifth Day of April, 1995

Attest:

BRUCE LEHMAN

Attesting Officer

*Commissioner of Patents and Trademarks*